United States Patent [19]

Takahashi et al.

[11] Patent Number: 5,249,366
[45] Date of Patent: Oct. 5, 1993

[54] DIMENSION MEASURING INSTRUMENT

[75] Inventors: Seigo Takahashi; Kouji Sasaki, both of Kawasaki, Japan

[73] Assignee: Mitutoyo Corporation, Tokyo, Japan

[21] Appl. No.: 874,613

[22] Filed: Apr. 27, 1992

[30] Foreign Application Priority Data

Apr. 26, 1991 [JP] Japan .................. 3-038991[U]

[51] Int. Cl.⁵ .................................. G01B 5/14
[52] U.S. Cl. ............................ 33/811; 33/784; 33/794; 33/512; 33/558.01
[58] Field of Search ............... 33/784, 810, 811, 812, 33/790, 512, 783, 791, 794, 795, 796, 797, 798, 799, 800, 801, 802, 828, 511, 558.01, 558.02, 558.03, 558.04, 558.05, 558.06, ; 33/558.07, 558.08, 558.09, 558.1, 558.2, 558.3, 558.4, 558.5

[56] References Cited

U.S. PATENT DOCUMENTS

| 1,424,492 | 8/1922 | Leschen ...................... 33/810 |
| 4,127,112 | 11/1978 | Sherlock et al. ............. 33/512 |
| 4,233,743 | 11/1980 | Flick .......................... 33/512 |
| 4,599,800 | 7/1986 | Wyrwich et al. ............. 33/512 |
| 4,612,656 | 9/1986 | Suzuki et al. ............... 33/784 |
| 5,022,162 | 6/1991 | Luikko ........................ 33/784 |
| 5,029,402 | 7/1991 | Lazecki et al. .............. 33/784 |

FOREIGN PATENT DOCUMENTS

| 3346273 | 7/1984 | Fed. Rep. of Germany ........ 33/784 |
| 0200643 | 5/1983 | German Democratic Rep. ... 33/810 |

Primary Examiner—Thomas B. Will
Attorney, Agent, or Firm—Flynn, Thiel, Boutell & Tanis

[57] ABSTRACT

A dimension measuring instrument has a main scale 2 and a slider 3 in a state to move relatively, each of the main scale 2 and the slider 3 having a jaw 4, 5. These jaws 4, 5 are provided with finger lay portions 7, 9 thereon, respectively. In a measurement procedure, a pair of jaws 4, 5 urged by figures held in the finger lay portions 7, 9 is reciprocally opened and closed without any spring to catch the object to be measured, of which arrangement is advantageous for simple structure and reasonable price of the instrument. In particular to a fat thickness measurement, the object portion can be almost held with fingers, so that the operator can perform by himself in the home.

8 Claims, 6 Drawing Sheets

DIMENSION MEASURING INSTRUMENT

BACKGROUND OF THE INVENTION

1. Field of the Invention

The present invention refers to an instrument of wide use for measuring dimension of parts of a machine, sorting fruit according to their sizes, making a measure of the human body fat thickness, especially to an instrument which can be used by any user with no assistance or specialist.

2. Description of the Related Art

Hitherto, a dial caliper gauge is a useful measuring instrument of wide fame for thickness or dimension measurement. It is common to apply the dial caliper gage to examine dimensions of industrial parts, to sort fruit according to their sizes, or to make a measure of the human body fat thickness at a medical organ such as a hospital or at a private sports club. The how of the measurement by the conventional dial caliper gauge is that an object to be measured is caught (=measuring force), by means of a spring provided in the caliper gauge, in a set of jaws, one of which being provided to a main scale and the other to a slider. In a measurement of the fat thickness, since the caliper user as a subject can not operate the caliper gauge by himself a specialist of measurement should be employed.

Recently, there is the general requirement of using a dimension measuring instrument like a dial caliper gauge not only at factories, fruit wholesale markets or medical organs but also at each home. But, such the conventional dial caliper gauge has limited uses and presents problems. As explained above, another person is indispensable for operation in the human fat thickness measurement and besides the conventional caliper gauge is rather big in size, expensive and difficult to operate in homes.

It is therefore expected to invent a dimension measuring instrument which allows free measurement of any object in homes and can be bought at a reasonable price.

An object of the present invention is to provide a dimension measuring instrument which can be obtained at a reasonable price and which users can operate by themselves without difficulty.

SUMMARY OF THE INVENTION

The dimension measuring instrument according to the present invention is made in view of a problem presented in the conventional instrument having a spring for the constant measuring force. The invented instrument can keep the same measuring force as in the conventional instrument by the operator's feeling when holding any object including his own fat or by a mechanical method.

An invented dimension measuring instrument according to the present invention has: a main scale; a slider associated with the main scale so as to along lateral direction of the main scale; measuring means for measuring relative displacement between the main scale and the slider; display means for indicating a measured value issued from the measuring means; a pair of jaws, of which one being provided at the main scale and the other being provided at the slider; and finger lay means provided at an outside of each of the jaws for keeping a finger to thereby move the jaws respectively, so that a measurement of the object is carried out with holding the object between the jaws.

The dimension measuring instrument may be provided with display control means for keeping and renewing a measured value on the display means under a certain condition.

Each of the jaws is preferably provided with a hole or a mechanical detector to obtain a certain measuring force. The detector can be replaced with a general switch capable of manual control.

A relative movement of a set of jaws can be made comfortable through measuring operation by means of a L-shaped support member, a guide groove, or a rubber band.

The display means may be integrated with or separately provided from the measuring instrument.

In an operation of the invented instrument, the operator's thumb and forefinger are inserted into the finger lay portions, respectively and an object to be measured is to be held by two finger power in a pair of jaws to thereby measure thickness or dimension of the object.

Accordingly, when measuring fat thickness of the operator as an object, the operator can complete a measuring by himself. Besides, the measuring force can be kept constant by the operator's feeling or mechanical means, so that the measurement can be done correctly with no spring, the structure becomes ease and the price of the instrument becomes reasonable.

DETAILED DESCRIPTION OF THE PREFERRED EMBODIMENT(S)

The followings are explanations of the first embodiment in the present invention with reference to the accompanied drawings on the assumption that an object to be measured by a dimension measuring instrument according to the present invention is to be the human fat thickness.

Figure 1:
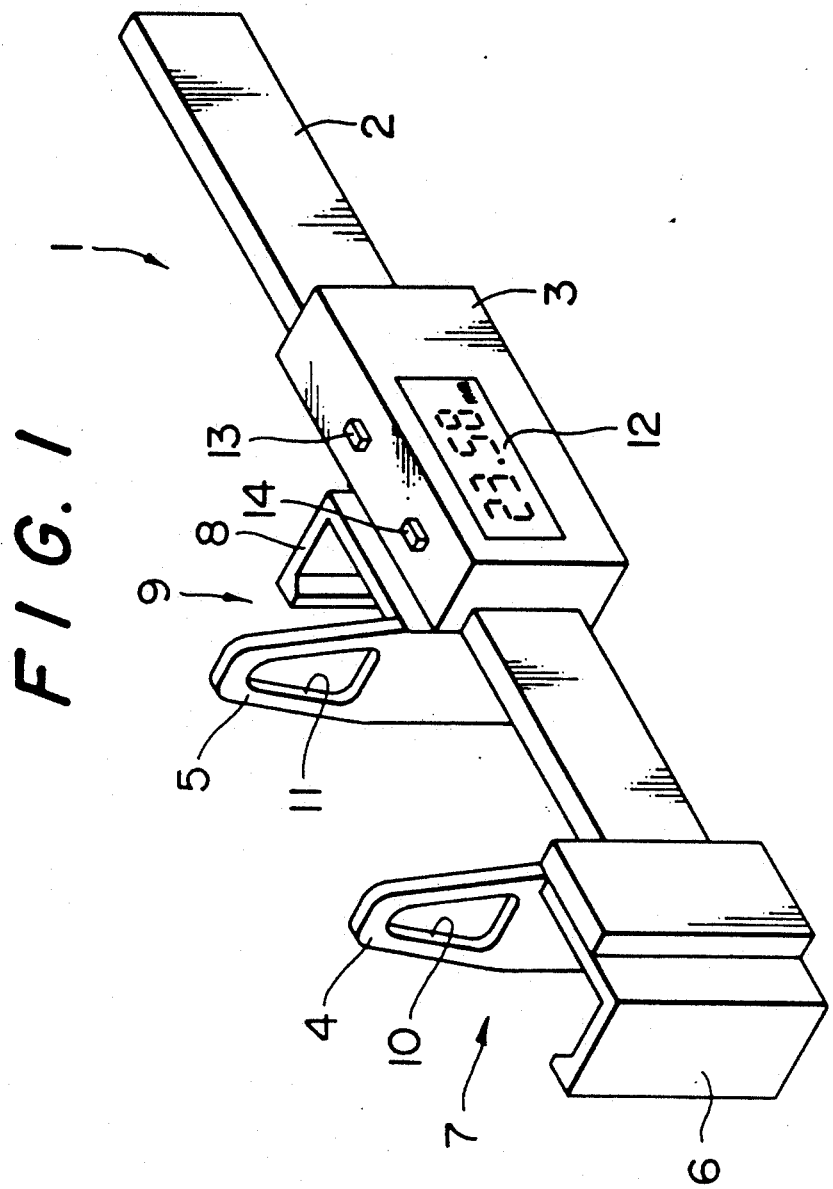
FIG. 1 is a perspective view of a dimension measuring instrument according to the present invention.

The dimension measuring instrument 1 has, as shown in FIG. 1, a main scale 2 and a slider 3 associated with the main scale 2 in a state to move along the longitudinal direction thereof. At one end of or lower left portion of the main scale 2 on FIG. 1, one half-member 4 of jaws is provided, and at the slider 3 the other half-member of jaws is mounted so as to close to each other.

The one half-member 4 of the jaws is accompanied with a L-shaped support member 6 at its out side or left side thereof on FIG. 1. The jaw 4 and the support member 6 constitute a finger lay portion 7. The jaw 5 is also accompanied with a L-shaped support member 8 at its out side or right side thereof on FIG. 1. The jaw 5 and the support member 8 constitute a finger lay portion 9. Each jaw 4 or 5 has a touch hole 10, 11 where inserted fingers 15, 16 into the finger lay portions 7, 9 can expose their cushions.

The slider 3 has a built-in electrostatic encoder for measuring relative displacement between the main scale 2 and the jaw 5 of the slider 3 and thereafter displaying a measured value at a digital display portion 12. The slider 3 further comprises two switches, one switch 13 being for power-on and reset of the display portion 12, the other switch 14 being for power-off.

The following is an explanation about how a subject person can measure his own fat thickness by himself with the dimension measuring instrument 1.

Figure 2:
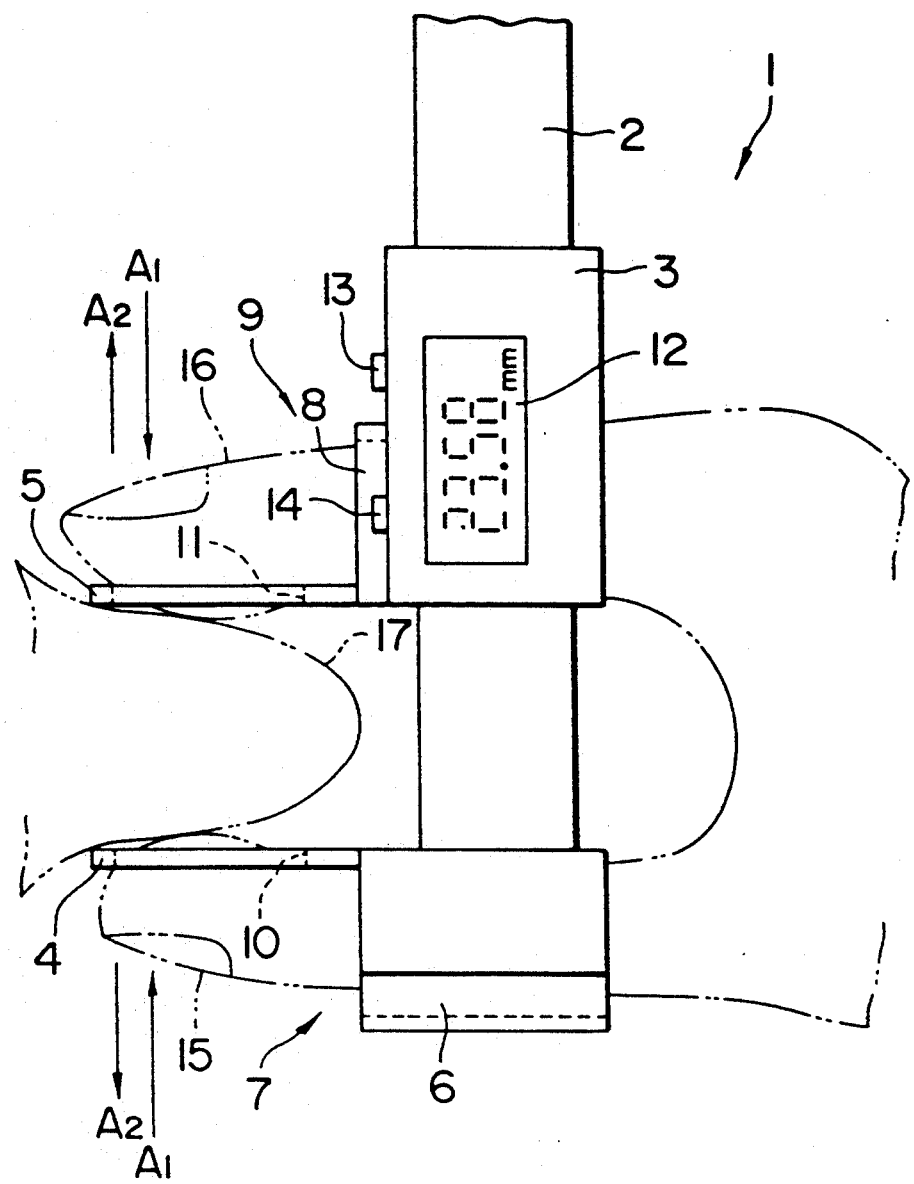
FIG. 2 is an enlarged plain view of the dimension measuring instrument.

After switching the instrument 1 on, the thumb 15 is inserted into the finger lay portion 7 while the forefinger 16 is inserted into the finger lay portion 9 as shown in FIG. 2. Both fingers 15, 16 are moved to the arrow A1 direction to close the jaws 4, 5. When entirely closed, the switch 13 is operated to reset the value on the display portion 12.

Subsequently, the fingers 15, 16 are oppositely moved to the arrow A2 direction to open the jaws 4, 5 enough and catch an object to be measured 17 such as human fat thickness at stomach or arm by moving the jaws 4, 5 to close to each other. The expected measuring value of the object 17 is displayed on the display portion 12, which can be read by the operator. The measuring force toward the each jaw 4, 5 is controlled by the feel of fingers 15, 16 exposed from the touch holes 10, 11 so as to touch the object 17 or by the direct feel from the object 17.

The jaws 4, 5 are thereafter moved to the arrow A2 direction for next measurement by fingers 15, 16, while the object 17 is dislocated. Finishing all the measurement, the power of the instrument 1 can be cut off by the switch 14. The above described embodiment produces a good effect on the operator.

Since the jaws 4, 5 are moved to catch the object 17 by thumb 15 and forefinger 16, the operator can measure his own fat thickness by himself with his two fingers 15, 16. Accordingly, the measuring process can be done easily, no specialist for measurement should be employed, and the operator as the object can execute measurement all alone.

The dimension measuring instrument according to the present invention does not need no spring as that in the conventional instrument because the jaws 4, 5 are moved by the fingers 15, 16 when catching the object 17, which may lead to simple structure and low price of the instrument 1, so that the instrument 1 can be used in homes.

In the present structure, the measuring force can be kept constant by the feeling of the fingers 15, 16 and the direct touching to the object 17 through the touch holes 10, 11 with the fingers 15, 16 can replace the spring used in the conventional dimension measuring instrument and perform precise measurement.

The measured value can be indicated by numerals on the display portion 12 of the slider 3, which is easy to read for any operator and leads to correct measurement of the fat thickness.

The touch holes 10, 11 of the jaws 4, 5 to directly touch to the object 17 in the above explained first embodiment of the present invention can replace notches at forwarded end portions of the jaws 4, 5 to thereby touch the two top points of the fingers 15, 16 to the object 17. But in view of a correct measurement, the contact of the fingers 15, 16 to the object 17 through the touch holes 10, 11 as explained in the first embodiment can lead to a good result because such touch can prevent the object 17 from slipping off the jaws 4, 5.

Figure 3:
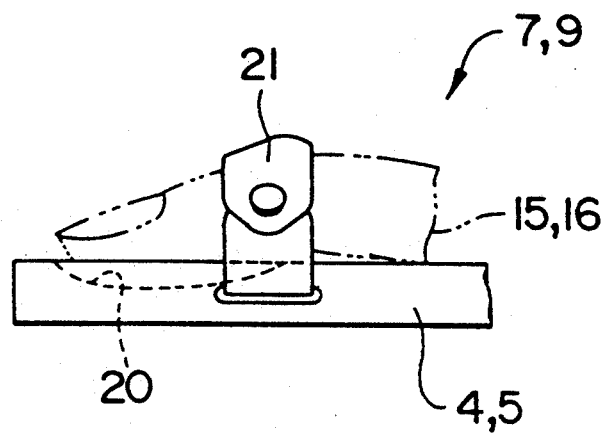
FIG. 3 is a perspective view of one modified arrangement of a finger lay portion.
Figure 4:
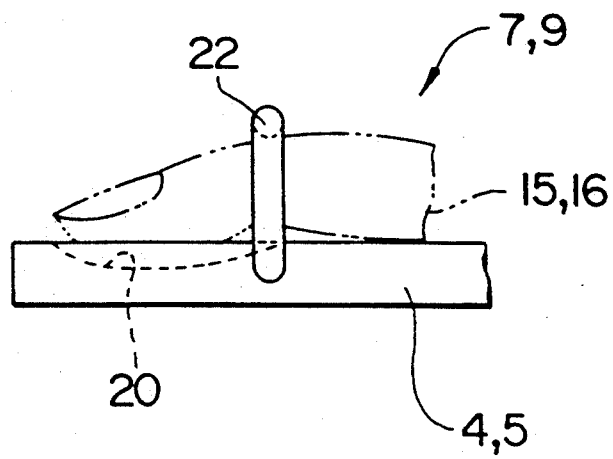
FIG. 4 is a perspective view of another modified arrangement of a finger lay portion.

Other modifications of the finger lay portions 7, 9 are shown in FIGS. 3, 4 in which the fingers 15, 16 are not touched to the object to be measured 17.

Shown finger lay portions 7, 9 have grooves 20, 20 on the jaws 4, 5 which formed into a shape to which the cushions of fingers 15, 16 can fit and further have ring members 21, 22 to transmit the movement of the fingers 15, 16 to the jaws 4, 5. The preferable ring member should be a elastic rubber band 21 with a button or a ring-shaped simple member 22. These finger lay portions 7, 9 are advantageous to weight control of and also comfortable use of the instrument because of less clearance between the fingers 15, 16 and the jaws 4, 5.

Figure 5:
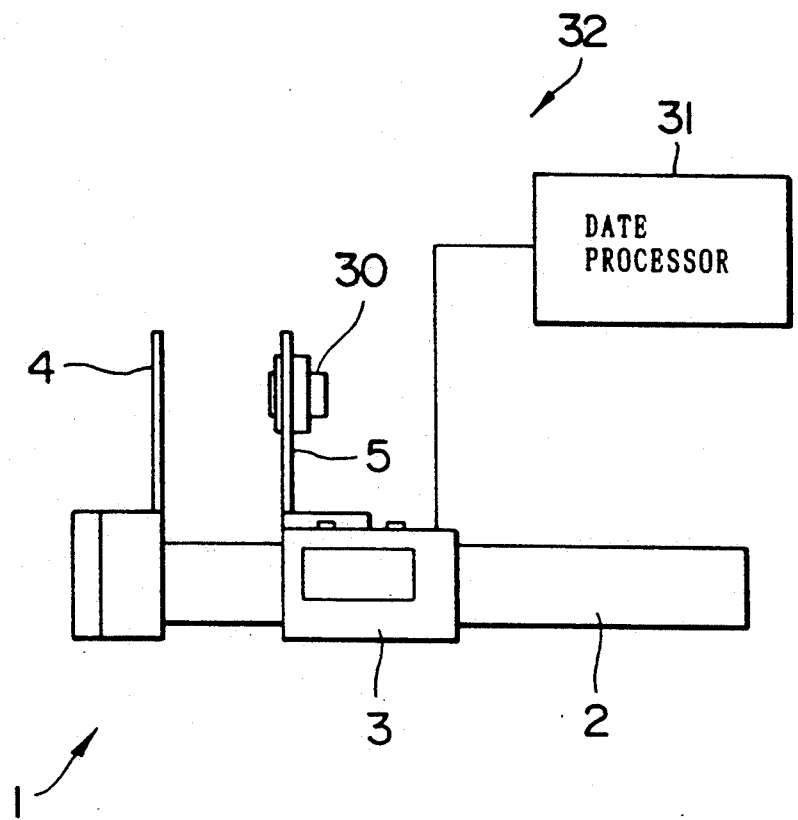
FIG. 5 is a conceptual view of the second embodiment of the present invention.
Figure 6:
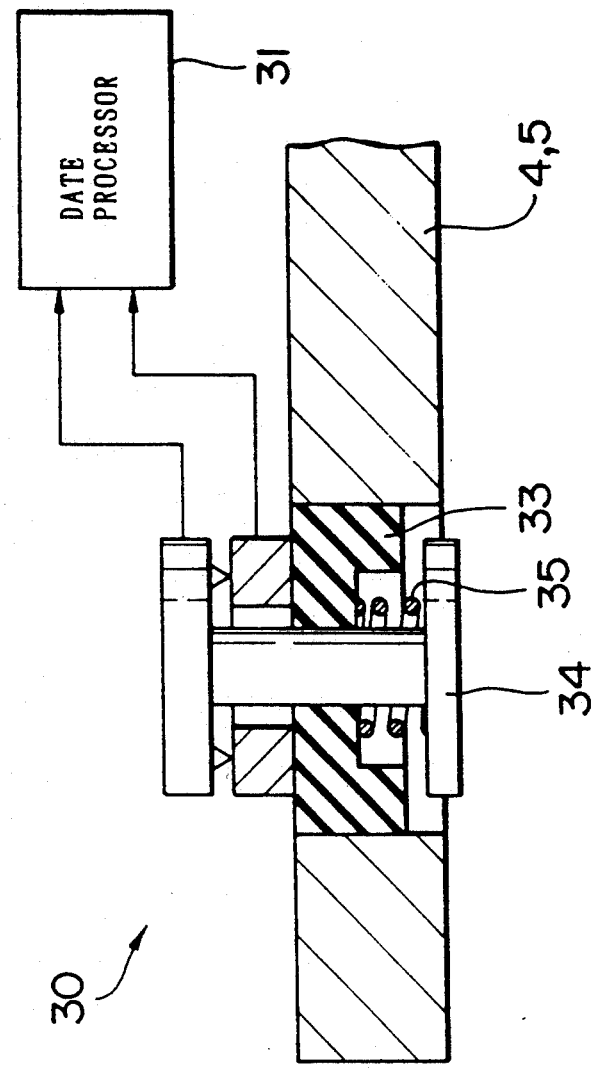
FIG. 6 is an enlarged plain view of a detector in the second embodiment.
Figure 7:
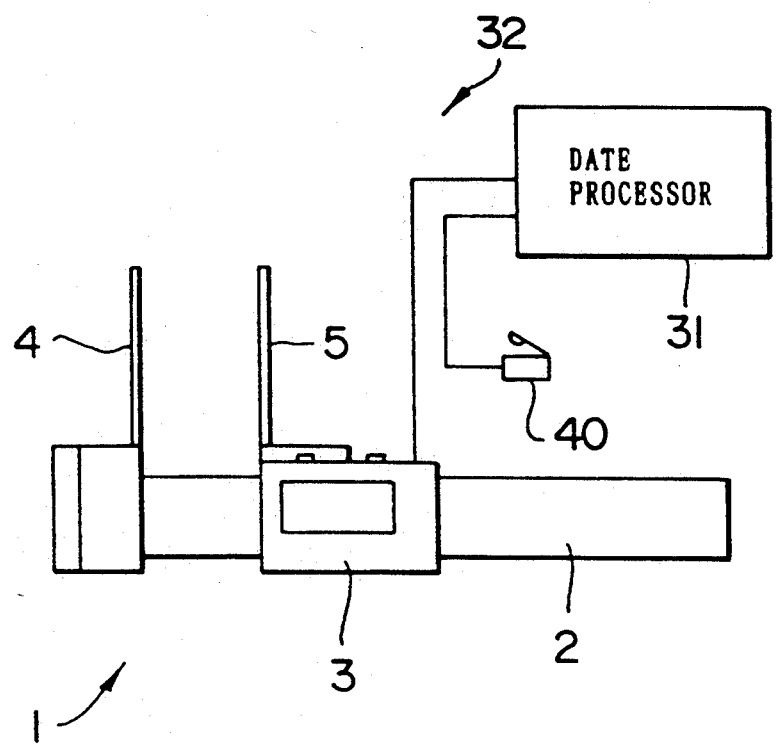
FIG. 7 is a conceptual view of a modified second embodiment.

The second embodiment of the present invention will be explained in detail with reference to FIGS. 5 to 7. In this embodiment, the dimension measuring instrument 1 further comprises a display control apparatus 32 for keeping and renewing a measured value on the display portion 12. The display control apparatus 32 essentially consists of at least one detector 30 provided at either the jaws 4, 5 and a data processor 31.

The detector 30 is provided at a forwarded portion of the jaw 4 or 5 with an insulator 33 lying therebetween, which is arranged to cut off the power by the object 17 abuts against a sensing plate 34 urged by a built-in spring 35. This electrical cut-off causes a pulse signal every motion of the sensing plate 34, which is transmitted to the data processor 31 by cable or radio. Accordingly, such electrical cut-off can replace the measuring force by means of the feeling from two fingers 15, 16 in the first embodiment, so that it is not always necessary to provide the touch holes 10, 11 or the notch portions at a portion of the jaw 4, 5. The data processor 31 to which the pulse signal is input functions to delete the displayed measured value on the display portion 12 and thereafter to display the present measured value as a new numeral value on the display portion 12 when the pulse signal is issued. The renewed value is kept until a next measurement. Accordingly, the repeated measurement for several objects to be measured can be realized.

Hence, in the second embodiment of the present invention, the measuring force toward the object by the fingers can be regulated by a certain force of the spring 35, which is advantageous for the measurement of the object under a constant measuring force without the feeling of the operator. These constant measuring force is particularly worth element for such objects as fruit being likely to be damaged easily. Another function of the data processor 31 except display is to record measured value, take statistics, or the like if necessary. Still another function of the data processor 31 is to process any measured value from other measuring instrument employed. Depending upon the circumstances, the dimension measuring instrument 1 used in the present invention can be replaced with another which is able to keep prior measured value and renew to a new value upon an issued pulse signal.

The detector 30 can be of another one like a piezoelectric element or the like. In case of no the detector 30, another display control apparatus 32 can be constituted, as shown in FIG. 7, by the same data processor 31 as in the explained embodiment and a hold switch 40 as a substitution for the detector 30, which is also useful array as that by the second embodiment. In an actual operation of this display control apparatus 32, when catching the object 17 in a set of the jaws 4, 5 with a certain measuring force, the hold switch 40 should be operated to effect an electrical cut-off as that by the detector 30.

Another modification of the data processor 31 in the present invention can be built in the instrument 1 to make it small in size. The hold switch 40 may be integrated with the slider 3. In this arrangement, a set of the jaws 4, 5 is controlled by thumb and middle finger while the hold switch 40 is operated by forefinger.

The present invention should be recognized as to include other embodiments and modifications capable of accomplishing the same purpose as explained so far.

For example, the display portion 12 has been integrated with the slider 3 in the first and second embodiments, but the display portion 12 can be prepared independently. Still another arrangement of the display portion 12 is to provide it to other portions such as support member 6 or 8 so as to notify easily. Yet another arrangement is not to provide but to borrow other display devices. Besides, the display portion 12 may be rotatably provided at the instrument 1 for both right-handed and southpaw operators.

Another encoder except the electrostatic type in the first and second embodiments is the photoelectric or contacting type. Of course, still another encoder can be employed if relative displacement between the main scale 2 and the slider 3 is measured.

As has been explained, the present invention can prevent unnecessary measuring force toward the object to be measured any time through measurement procedure and is preferable for the operator as an object to measure his own fat thickness without any assistant, so that the instrument can be bought at reasonable price for general use.

What is claimed is:

1. A dimension measuring instrument, comprising: a first member and a second member supported for relative movement, measuring means cooperable with said first and second members for measuring relative displacement therebetween and for providing an operator perceptible indication of the relative displacement, first and second jaws each provided on a respective one of said members and each engagable on a side thereof remote from the other by a finger, each of said jaws having a hole therethrough so that a cushion of a finger engaging the jaw projects through the hole therein toward the other of said jaws.

2. An instrument according to claim 1, including two L-shaped supports which are each provided on a respective one of said first and second members and which each have a first leg spaced from a respective said jaw on a side thereof remote from the other jaw and having a second leg secured to the member on which the L-shaped support is provided and extending from said first leg toward the jaw.

3. An instrument according to claim 1, wherein said first member is elongate and said second member is a slider movably supported thereon, and wherein said measuring means is provided on said slider, and includes digital display means for providing a digital display of the relative displacement.

4. A dimension measuring instrument, comprising: a first member and a second member supported for relative movement, measuring means cooperable with said first and second members for measuring relative displacement therebetween and for providing an operator perceptible indication of the relative displacement, and two jaws which are each supported on a respective one of said members and which each have on a side thereof remote from the other thereof a recess shaped to receive a fingertip and retaining means for resisting movement of a fingertip out of the recess.

5. An instrument according to claim 4, wherein said retaining means includes a respective ring mounted on each said jaw on a side thereof remote from the other of said jaws.

6. An instrument according to claim 4, wherein said retaining means includes a respective loop provided on each said jaw on a side thereof remote from the other thereof, each said loop being made of a resilient material.

7. An instrument according to claim 6, wherein said loop has two end portions secured to each other by a button.

8. An instrument according to claim 4, wherein said first member is elongate and said second member is a slider supported for movement therealong, and wherein said measuring means as provided on said slider, and includes digital display means for providing a digital display of the measured displacement value.

* * * * *